(12) United States Patent
Hough et al.

(10) Patent No.: US 6,245,324 B1
(45) Date of Patent: Jun. 12, 2001

(54) ANTIPERSPIRANT MATERIAL AND COMPOSITIONS CONTAINING IT

(75) Inventors: Gordon Charles Hough, Bebington (GB); David Terence Parrott, Chicago, IL (US); John Harold Rennie, Chester (GB)

(73) Assignee: Unilever Home & Personal Care USA, Division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/388,699

(22) Filed: Sep. 2, 1999

(30) Foreign Application Priority Data

Sep. 4, 1998 (GB) .................................................. 9819366

(51) Int. Cl.[7] .............................. A61K 7/32; A61K 7/34; A61K 7/36; A61K 7/38; A61K 7/00
(52) U.S. Cl. ................................ 424/65; 424/66; 424/67; 424/68; 424/400; 424/401
(58) Field of Search ................................. 424/65, 66, 67, 424/68, 400, 401

(56) References Cited

U.S. PATENT DOCUMENTS

| | | | |
|---|---|---|---|
| 4,078,051 | 3/1978 | Pomot et al. | 424/68 |
| 4,183,911 | 1/1980 | Smithies et al. | 424/36 |
| 4,318,843 | 3/1982 | Kohler et al. | 523/212 |
| 5,573,753 | 11/1996 | Tapley | 424/59 |
| 5,695,747 | * 12/1997 | Forestier et al. | 424/59 |
| 5,776,440 | 7/1998 | Forestier et al. | 424/59 |

FOREIGN PATENT DOCUMENTS

| | | |
|---|---|---|
| 22 41 030 | 8/1972 | (DE) . |
| 24 05 216 | 2/1974 | (DE) . |
| 0 021 262 | 6/1979 | (EP) . |
| 0 559 319 | 9/1993 | (EP) . |
| 0 832 639 | 9/1996 | (EP) . |
| 1391448 | 4/1975 | (GB) . |
| 1 602 428 | 6/1977 | (GB) . |

OTHER PUBLICATIONS

International Search Report Application No. PCT/EP 99/05613 mailed Dec. 3, 1999.

* cited by examiner

Primary Examiner—Shelley A. Dodson
(74) Attorney, Agent, or Firm—Mathew Boxer

(57) ABSTRACT

A particulate antiperspirant active material which has been surface treated with an alkanolamine is described. After surface treatment, the surface treatment agent is in intimate contact with the surface or outer layer of the substrate material, that is, the antiperspirant material may be either deposited on the surface or at least a fraction of the agent may be absorbed within the outer layer of the substrate. The resultant particulate material shows a reduced tendency to separate from a liquid carrier phase containing a polyglycol ether and a suspending agent.

32 Claims, No Drawings

ANTIPERSPIRANT MATERIAL AND COMPOSITIONS CONTAINING IT

The present invention relates to an antiperspirant material, a process for its preparation and to antiperspirant compositions containing it.

TECHNICAL FIELD BACKGROUND AND PRIOR ART

In a significant fraction of antiperspirant compositions, the active antiperspirant material is present in particulate form. For ease of dispensation, in many of such compositions, the active antiperspirant material is suspended or otherwise dispersed in a liquid carrier phase, often with the assistance of suspension agents or aids. If the antiperspirant material is not suitably suspended, there is a risk that it will tend to separate from the liquid carrier, for example by settling on the bottom of the container for the composition during storage or between applications. When the settled material can be readily redispersed by the user, such as by manual shaking of the applicator before use, solids settling constitutes a minor inconvenience rather than a significant problem. However, when the settling produces a compact layer which is extremely difficult or even impossible to redisperse manually, the problem attains serious proportions, because is extremely desirable to avoid or reduce the effective loss from the formulation of active antiperspirant material. Self-evidently, loss of active material during storage renders the composition non-uniform in application, with the risk that for a fraction of the time that the composition is used, it will be ineffective or insufficiently effective at controlling perspiration loss.

It has been found that advantageous skin sensory properties can be achieved by incorporating a polyglycol ether as at least part of the liquid phase in an antiperspirant composition. A practical way of suspending a particulate antiperspirant in a liquid carrier has comprised the incorporation of a suspending aid, often inorganic such as a clay. However, it has further been found that when the carrier comprises a polyglycol ether, the ability of the clay or like suspending agent to suspend or re-suspend the particulate antiperspirant material in the carrier liquid is significantly impaired.

It is known to surface treat particulate inorganic substances in other fields of activity, specifically pigments and sunscreens, but for other purposes. Thus, for example, titanium dioxide pigments are surface treated in GB-A-1602428 with esters or amines and this affects the rate at which films containing the pigment dry. In EP-A-0559319, metallic oxide particles, especially titanium dioxide and zinc oxide particles are surface coated to aid their suspension in aqueous emulsions. This is not relevant to predominantly anhydrous compositions of the present invention. Similarly in U.S. Pat. No. 5,573,753, dispersions of surface treated particulate titanium oxide and zinc oxide in an aqueous emulsion are described. In U.S. Pat. No. 4,318,843 (EP-A-0021262) there is described the surface treatment of inorganic pigments of which $TiO_2$ is exemplified in order to improve its gloss and distribution in lacquer bindings. In U.S. Pat. No. 5,776,440, the effectiveness of metallic oxide to screen out UV-radiation when applied topically is enhanced by coated them with a wide range of organic compounds. The treatment of TiO2 is exemplified.

It is an object of the present invention to ameliorate or overcome one or more of the problems or disadvantages indicated hereinabove.

SUMMARY OF THE INVENTION

According to the present invention there is provided a particulate antiperspirant material which has been surface treated with an alkanolamine.

According to related aspect of the present invention there is provided a process for surface treating a particulate antiperspirant material characterised by bringing the antiperspirant material into contact with an alkanolamine in a liquid medium and maintaining contact until at least some alkanolamine is deposited on or absorbed in the surface of the antiperspirant material.

By surface treating the particulate antiperspirant material with the alkanolamine, it has been found that the resultant particulate material shows a reduced tendency to separate from a liquid carrier phase containing a polyglycol ether and a suspending agent.

Surface treating and surface treatment herein indicates that the surface treatment agent is in intimate contact with the surface or outer layer of the substrate material, i.e. the antiperspirant material, and may either be deposited on the surface, for example forming a layer or coating of the treatment agent on the substrate surface or at least a fraction of the agent may be absorbed within the outer layer of the substrate.

In a further aspect of the present invention, there is provided an antiperspirant composition comprising an antiperspirant material and a liquid phase comprising a carrier characterised in that the antiperspirant material comprises a particulate antiperspirant material which has been surface treated with an alkanolamine.

Herein, comprising in the context of a composition indicates that the composition may contain one or more further ingredients in addition to those specified within the composition.

DETAILED DESCRIPTION OF THE INVENTION

The invention provides a particulate surface treated antiperspirant active and antiperspirant compositions containing the same, and especially compositions containing a polyglycol ether and a suspending agent.

Antiperspirant Material

The antiperspirant material can comprise any particulate material which is capable of reducing or preventing perspiration when it is applied topically to human skin. The present invention is directed to antiperspirant actives which when applied topically penetrate the eccrine gland and are subsequently deposited therein, blocking its duct and preventing egress of sweat. Accordingly, such material commonly comprises an astringent salt. The antiperspirant often comprises aluminium, zirconium, mixed aluminium/zirconium salts, and titanium salts, including both inorganic salts and organic salts and complexes. Preferred astringent salts include aluminium, zirconium and aluminium/zirconium halides and halohydrate salts, such as chlorohydrates. Some especially preferred halohydrate salts comprise activated aluminium chlorohydrates such as those described in EP-A-6739 (Unilever NV et al) and other actives are described in EP-A-28853, the contents of both specifications being incorporated herein by reference. It will be recognised that metallic oxides derived from aluminium, zirconium, titanium or zinc are considered not to be antiperspirants.

Astringent aluminium salts include aluminium chloride and aluminium halohydrates having the general formula $Al_2(OH)_xQ_y \cdot XH_2O$ in which Q represents chlorine, bromine or iodine, x is from 2 to 5 and x+y=6, x and y being either integers or non-integers and X being from 0 to 6.

A range of zirconium salts which can be employed in antiperspirant compositions herein is represented by the following empirical general formula: $ZrO(OH)_{2n-nz}B_z$ in which z is an integer or non-integer in the range of from 0.9 to 2.0, n is the valency of B, 2–nZ is at least 0 and B is selected from the group consisting of halides, including chloride, sulphamate, sulphate and mixtures thereof.

It will be recognised that the above-identified formulae for aluminium and zirconium salts are greatly simplified and encompass compounds having co-ordinated and/or bound water in various quantities as well as polymeric species and mixtures and complexes.

Antiperspirant complexes based on the above-mentioned astringent salts are known and employable in the present invention. By way of example, complexes of aluminium, zirconium and aminoacids such as glycine are disclosed in U.S. Pat. No. 3,792,068 (Luedders et al). Certain of those complexes or complexes with related structures are commonly called ZAG in the literature. One desirable class of complexes which exhibit structure like ZAG comprise aluminium chlorohydrate, including that satisfying the formula $Al(OH)_5Cl.2H_2O$ complexed with aminoacids or other complexing agents. A preferred class of zirconium-based complexes which exhibit structures like ZAG comprise zirconylchlorohydrate of empirical formula $ZrO(OH)_{2-a}Cl_2.nH_2O$ in which a is a non-integer in the range of from 1.5 to 1.87 and n is from 1 to 7 complexed with amino acids or other complexing agents. Activated ZAG complexes can be employed as antiperspirant active in the present invention, such as the materials disclosed in U.S. Pat. No. 5,486,347 (Callaghan et al).

Other actives which can be contemplated for employment as appropriate in compositions produced and/or dispensed in accordance with the present invention comprise particulate titanium salts such as hydroxycarboxylates, e.g. citrate or lacteate.

Particularly when the antiperspirant salt is intended to be applied in an aerosol, it is preferable to employ a zirconium-free salt, such as an aluminium salt or possibly a titanium salt, including especially aluminium chlorohydrates (ACH) and activated aluminium chlorohydrates (AACH).

The particle size of antiperspirant salts employed herein often falls within the range of 1 to 200 micrometers. In many desirable formulations, and especially for application by an aerosol, the mean particle size of the antiperspirant salt falls within the range of from 5 to 50 $\mu$m and especially from 15 to 30 $\mu$m.

Alkanolamine

The alkanolamine can comprise an aliphatic compound containing both an amine and an hydroxyl function. It desirably has a low molecular weight, for example containing up to 12 carbon atoms, which can include a linear or branched alkyl group. The alkanol moiety preferably comprises a $C_3$ or $C_4$ alkyl group, as in hydroxypropylamine or hydroxybutylamine. The amine can be primary, secondary or tertiary. All of the amine substituents can comprise alkanol substituents, or in secondary amines or in tertiary amines, respectively one or either one or two of the substituents can comprise a an alkyl group, such as $C_1$ to $C_4$. Examples of a primary amine include propanolamine, secondary amine include methyl propanolamine and examples of a tertiary amine include triisopropanolamine. In many instances, the alkanolamine comprises a single amine and in other instances comprises from 1 to 3 hydroxyl groups, though normally not more than two hydroxyl substituents in any particular alkanol group. A mixture of two or more of such alkanolamines can also be employed. The antiperspirant material can conveniently be surface treated by bringing it into contact with the alkanolamine in fluid form. For example the alkanolamine can be heated to above its melting point, where necessary, or dissolved in a suitable solvent. The solvent can comprise a hydrophobic liquid such as a silicone oil or a hydrocarbon oil. The antiperspirant and alkanolamine are desirably left in contact until a desired weight of the alkanolamine has been retained by the antiperspirant, normally as a surface layer on or coating of the antiperspirant or absorbed within the outer layer of the antiperspirant. Where the alkanolamine is applied to the antiperspirant in solution, the solution can, if desired, be allowed to remain permanently in contact with the antiperspirant, instead of being separated when the antiperspirant carried a desired amount of the alkanolamine, in which case the solvent for the alkanolamine subsequently functions as a liquid carrier or a component thereof in an antiperspirant composition. In such compositions, a fraction of the alkanolamine may remain within the liquid carrier.

It will be recognised that the surface treatment of the antiperspirant solid can be carried out as a separate step, for example before the antiperspirant active is incorporated into an antiperspirant composition, or can form in situ provided that the composition contains both the alkanolamine and antiperspirant active in a fluid medium that enables them to come into contact with each other.

The antiperspirant material is normally brought into contact with from 0.2 to 8% by weight of the alkanolamine, and in many instances the proportion of alkanolamine is selected in the range of from 0.4 to 2.5% by weight, based on the weight of the antiperspirant. An especially convenient range can be from 0.75 to 1.5% by weight of alkanolamine based on the antiperspirant.

The surface treated antiperspirant material is frequently incorporated in a composition comprising a liquid carrier. The proportion of antiperspirant material is normally calculated by weight on an anhydrous salt basis, i.e. excluding the weight of any hydrated water or complexing agent that may also be present and excluding the weight of any surface treatment.

Liquid Carrier

In an important aspect of the present invention, the liquid carrier comprises a polyglycol ether, the latter preferably constituting from 5 to 95% by weight of the liquid phase, particularly from 30 to 75% and especially from 40 to 60%. Such a composition represents a convenient base composition which is capable of being employed by itself or of serving as a base composition to which further constituents can be added, for example to create an aerosol composition. The presence of the polyglycol ether imparts advantageous emollient properties, and can lower visible deposits when the composition is topically applied to human skin.

The polyglycol ether usually is derived from a low molecular weight glycol, frequently a $C_2$ to $C_4$ glycol, such as from ethylene, propylene or butylene glycol and is especially a polypropylene glycol ether. The polyglycol moiety desirably contains from 5 to 24 glycol units and in a number of preferred ethers contains from 10 to 16 glycol units, especially 10 to 16 propylene glycol units. The ether moiety is preferably aliphatic, derivable from a low molecular weight aliphatic alcohol and especially an alkanol containing up to 8 carbons, particularly 3 to 8 carbons. The alkanol is frequently propanol or butanol. Polypropylene glycol butyl ethers in which the polyglycol moiety contains 10 to 16 propylene glycol units, e.g. 13 or 14, are particularly suitable.

In practice, it is desirable to select the proportions of the polyglycol ether and the alkanolamine, both as described hereinbefore, in the composition to fall within a weight ratio of 20:1 to 150:1, particularly 30:1 to 120:1 and preferably 45:1 to 80:1.

By selecting the relative proportions of polyglycol ether and alkanolamine within the above-identified ratio ranges and especially within the preferable range, it is possible to improve the suspension of the particulate antiperspirant material in polyglycol ether carrier fluids in the presence of a suspending agent. In the absence of the alkanolamine, there is a tendency in such compositions for layers of the particulate material to settle out during storage which are extremely difficult or impossible to redisperse by manual shaking. By incorporating the alkanolamine, such as by bringing it into intimate contact with the antiperspirant, it is possible to inhibit or substantially eliminate the tendency of such very poorly redispersible layers to form. To the extent that some or all of the particulate material does settle out, it can be more readily redispersed, for example by manual shaking, when the alkanolamine is incorporated in composition.

It will be recognised that the alkanolamine can be present in the composition as a surface treatment on the antiperspirant material and also that a fraction of it can remain in solution in the liquid carrier.

In a number of particularly desired embodiments of the present invention, there is provided an antiperspirant composition comprising a particulate antiperspirant material, an alkanolamine a liquid carrier comprising a polyglycol ether and a suspending agent.

Suspending Agent

In such a composition, the suspending agent is suitably inorganic, and is particularly a clay or a silica. The clay is often a montmorillonite, and advantageously can have been surface treated with an organic material such as an amine to render it hydrophobic. Examples of montmorillonites include bentonites, hectorites and colloidal magnesium aluminium silicates. Particularly suitable surface treated clays comprise surface treated bentonites which are available under the trademark Bentone from Rheox, such as Bentone 27, Bentone 34 Bentone 38 and Bentone LT. Suitable silicas include fumed silicas and particularly those of very fine particle size, such as those available under the trademarks Cab-o-sil and AEROSIL. It is especially desirable that the suspension agent is a hydrophobically surface treated clay.

The suspending agent is often incorporated in an amount of from 0.1 to 15% by weight of the compositions described herein and in particular in an amount of from 3 to 10% of base compositions, i.e. compositions comprising solely antiperspirant active, carrier liquid, alkanolamine and suspending agent before being formulated with for example a propellant to produce an aerosol. In preferred formulations according to the present invention, the weight ratio of antiperspirant to suspending agent is often selected in the range of from 2.5:1 to 20:1.

Other Constituents

The liquid carrier is normally anhydrous, that is to say does not contain any free water and particularly does not contain an aqueous phase. In practice, this means that formulations containing such carriers are anhydrous. In addition to the polyglycol ether, the liquid carrier can additionally comprise one or more hydrophobic fluids, including silicone oils, and liquid hydrocarbons. The liquid carrier often comprises from 5 to 80% by weight of the composition. Where the composition constitutes a base composition which is intended to be augmented with propellant to form an aerosol composition, the proportion of liquid carrier is particularly from 30 to 70% by weight of the base composition. The liquid carrier or mixture of carriers often constitutes 70 to 99% and particularly 80 to 95% of the liquid phase in the base composition, recognising that liquid constituents which are incorporated as emollients also function as carriers. The ratio of polyglycol ether to the total of other carriers in the compositions is often selected in the range of from 10:1 to 1:10, and in many preferred compositions is in the range of 2:1:1:2.

Silicone oils are preferred constituents of the composition and such oils employable herein are normally chosen from polysiloxanes and particularly polyalkylsiloxanes, or from silicone glycols. The oils can be either volatile or non-volatile or a mixture of both, but preferably volatile oils constitute the major proportion of silicone oils.

Volatile silicones are often chosen from cyclic polysiloxanes of formula —[—SiRR'—]$_n$— in which R and R' represent an alkyl, preferably a methyl group and n is from 3 to 8 and especially 4 or 5, otherwise referred to as cyclomethicones. Other suitable volatile silicones can be selected from low molecular weight linear polysiloxanes of formula SiRR'R"—[—SiRR'—]$_m$—SiRR'R" in which R R' and R" each represent an alkyl, preferably a methyl group and m is from 1 to 7 and especially 2 or 3. The volatile silicone oils generally have a viscosity of from about 1 to 10 centistokes at 25° C. Examples of volatile silicones are Dow Corning 225, 244, 245, 344, 345, 1732, 5732, 5750, (all available from the Dow Corning Corp.) and Silicone GE7207, GE7158, SF1202, SF1173, SF-96 and SF-1066 (all available from General Electric Co [USA]).

Non-volatile silicone oils which are suitable for incorporation in compositions herein can comprise polyalkylsiloxanes, polyalkarylsiloxanes or polyether siloxane copolymers, typically having a viscosity of above 10 centistokes at 25° C. Many non-volatile silicone oils have a viscosity often up to about 2000 centistokes, and others have a still higher viscosity, such as up to about $10^6$ to $5 \times 10^6$ centistokes. Examples of suitable non-volatile polyalkylsiloxanes are available from Dow Corning under the 200 series. Suitable polyalkarylsiloxanes comprise polymethylphenylsiloxanes having a viscosity of from about 15 to 65 censtistoke at 25° C., such as those available from Dow Corning as 556 fluid. Suitable polyether siloxanes comprise dimethylpolyoxyalkalene ether copolymers (dimethicone copolymers) which often have a viscosity of from 1200 to 1500 censtistoke at 25° C., such as a polysiloxane ethylene glycol ether copolymer. Yet other suitable non-volatile silicone oils comprise or contain dimethicone/alcohol polymers (dimethiconols).

The liquid carrier can comprise, if desired a liquid hydrocarbon, such as a mineral oil, paraffin oils, petrolatum or hydrocarbon oils.

The liquid phase of compositions herein can additionally comprise other liquid emollients, such as liquid esters often containing from about 12 to 25 carbons which contain a long chain (usually containing at least 12 carbons) and short chain alkyl group (usually containing from 2 to 6 carbons), derivable from an acid and alcohol, or vice versa, such as isopropyl myristate or palmitate. Other suitable esters comprise short chain alkyl esters of aryl di or tri carboxylic acids, such as diethyl or dibutyl phthalate. Other liquid emollients include liquid fatty alcohols, often having a molecular weight of from about 200 to 350, such as octyldodecanol or isocetyl alcohol.

The composition can additionally comprise one or more suspension assistants, for example propylene carbonate, and in an amount of from 0 to 50% by weight of the suspension agent. Other optional constituents of the composition comprise an antioxidant or preservative, which sometimes comprises from 0 to 0.5%, particularly from 0.01 to 0.15% by weight of the composition.

An important, though optional, constituent of many antiperspirant compositions according to the present invention is a fragrance. The fragrance can be incorporated in oil-soluble form and/or be encapsulated. In many of the invention compositions, the fragrance comprises 0.1 to 3% by weight. In base formulations, i.e. those intended to be diluted e.g. with liquified propellant, the fragrance can often represent a relatively high proportion, such as from 1.5 to 8%.

Additional optional constituents of the composition can comprise a particulate filler, preferably impalpable, such as talc or a microfine starch or starch succinate derivative (Dry Flo™) or a very fine particulate polyethylene (Acumist™), and conveniently in an amount of from 0 to 20% of a base composition, and particularly in dispensed formulations of from 0 to 5%. A further optional constituent can comprise a microbicide, such as a bactericide, which in some compositions is incorporated in an amount of from 0.1 to 1% by weight. Suitable microbicides include biguanide salts such as available under the trademark Cosmosil™ and chlorinated aromatics, including chlorinated phenyl ethers and biguanide derivatives, of which materials known as Triclosan, Triclorban™ and Chlorhexidine warrant specific mention.

The antiperspirant compositions described herein can be made by mixing the constituents, for example using conventional apparatus for mixing a particulate material with one or more liquids. They are particularly suited for application via a spray, or by a roll-on.

Aerosol Formulations

In one especially desirable aspect of the present invention, the compositions above described are diluted with a propellant to form an aerosol formulation. The aerosol formulation often comprises from 40 to 99 parts by weight, and particularly 50 to 95 parts by weight propellant and the remainder (respectively 60 to 1 and particularly 50 to 5 parts by weight) the antiperspirant base composition.

The propellant is normally selected from liquified hydrocarbon or halogenated hydrocarbon gasses which have a boiling point of below 10° C. and especially those with a boiling point below 0° C. It is especially preferred to employ liquified hydrocarbon gasses, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane.

Other propellants which can be contemplated include alkyl ethers, such as dimethyl ether or compressed non-reactive gasses such air, nitrogen or carbon dioxide.

The aerosol formulation can incorporate, if desired, anti-clogging agents in conventional amounts, in order to prevent of minimise the occurrence of solid occlusions in the spray nozzle.

The aerosol formulation is usually filled into an aerosol canister that is capable of withstanding pressures generated by the formulation, employing conventional filling apparatus and conditions. The canister can conveniently be a metal canister commercially available fitted with a dip tube, valve and spray nozzle through which the formulation is dispensed.

The antiperspirant compositions according to the present invention can be applied topically to human skin, in order to control perspiration Having described the invention in general terms, specific embodiments thereof are now described in greater detail by way of example only.

EXAMPLE 1

In this Example, a surface treated particulate antiperspirant material is obtained by introducing activated aluminium chlorohydrate (hereinafter AACH) (100 g) which has been obtained by heating aluminium chlorohydrate having a suitable formula under suitably controlled conditions, having a particle size of 10 to 70 μm into a vessel equipped with agitation means. Thereafter, molten methyl propanolamine (1 g) is added and mixed thoroughly with the AACH for a period of a few minutes. The resultant product consists of AACH which has been surface treated with methyl propanolamine.

EXAMPLES 2 TO 8

In each of these Examples, a base composition is obtained which is suitable for dilution with propellant to form an aerosol composition employing a conventional method for mixing a particulate constituent with liquid constituents. The compositions are as summarised in Table 1 below:

| | Percent by weight Example No | | | | | | |
|---|---|---|---|---|---|---|---|
| Constituent | 2 | 3 | 4 | 5 | 6 | 7 | 8 |
| AACH | 40 | | 38.46 | 10 | 30.8 | 40 | 38.5 |
| ACH | | 48 | | | | | |
| hydrophobic clay (Bentone 27) | | | 7.7 | | 3.9 | | |
| hydrophobic clay (Bentone 38) | 4 | 4.8 | | 3.5 | | 4 | 3.8 |
| PPG13 butyl ether (Fluid AP) | 24 | 20.76 | 23.07 | 50 | 27 | 24 | 23.1 |
| Methylpropanol-)amine (AMP 100) | 0.4 | 0.44 | 0.39 | 0.4 | 0.4 | 0.4 | 0.4 |
| Volatile silicone (DC245) | 28 | 22 | | | | 28.2 | 27.7 |
| Volatile silicone (DC345) | | | 24.23 | | | | |
| Volatile silicone (DC1465) | | | | 29.55 | | | |
| Volatile silicone (DC246) | | | | | 34.8 | | |
| Fumed silica (AER-O-SIL 200) | 0.4 | | | 0.05 | | | |
| Octyldodecanol | 1.2 | | | | | | |
| isopropymyristate | | | | | 0.8 | | |
| Propylene carbonater | | | 0.77 | | | | |
| Polydecene (Silkflo 364) | | | | 1.5 | | | |
| Diethyl phthalate | | | | | 0.4 | | |
| Silicone gum (Q2-1501) | | | | | | 0.8 | 1.5 |
| fragrance | 2 | 4 | 5.38 | 5 | 1.9 | 2.6 | 5 |

The compositions described in Table 1 demonstrated good resistance to formation of a settled compacted solids layer and a good capability of settled solids to redisperse when subjected to manual shaking.

EXAMPLES 9 TO 15

In these Examples, aerosol formulations were obtained by diluting the base compositions described in Table 1 with a liquified hydrocarbon propellant using conventional methods. The formulations were filled into conventional blown aluminium aerosol canisters fitted with dipstick, flow valve and spray head. The aerosol formulations are summarised in Table 2 below. CAP40 is a mixture of butane, isobutane and propane.

TABLE 2

| | Percent by weight Example No | | | | | | |
|---|---|---|---|---|---|---|---|
| | 9 | 10 | 11 | 12 | 13 | 14 | 15 |
| Propellant (CAP 40) | 75 | 75 | 87 | 80 | 74.1 | 75 | 87 |
| Composition of Ex2 | 25 | | | | | | |
| Composition of Ex3 | | 25 | | | | | |
| Composition of Ex4 | | | 13 | | | | |
| Composition of Ex5 | | | | 20 | | | |
| Composition of Ex6 | | | | | 25.9 | | |
| Composition of Ex7 | | | | | | 25 | |
| Composition of Ex8 | | | | | | | 13 |

What is claimed is:

1. A particulate antiperspirant material which has been surface treated with an alkanolamine.

2. An antiperspirant material according to claim 1 wherein the alkanolamine comprises a C1 to C8 alkanol.

3. An antiperspirant material according to claim 2 wherein the alkanol is propanol or butanol.

4. An antiperspirant material according to claim 1 wherein the alkanolamine is a secondary amine.

5. An antiperspirant material according to claim 4 wherein the alkanolamine is methylpropanolamine.

6. An antiperspirant material according to claim 1 wherein the particulate material supports from 0.2% to 8% by weight of the alkanolamine.

7. An antiperspirant material according to claim 6 wherein the particulate material supports from 0.4% to 2.5% by weight of the alkanolamine.

8. An antiperspirant material according to claim 1 wherein the particulate material comprises an astringent compound of aluminium, zirconium, mixed aluminium/zirconium or titanium.

9. An antiperspirant material according to claim 7 wherein the astringent compound comprises an aluminium chlorohydrate or an activated aluminium chlorohydrate.

10. An antiperspirant material according to claim 1 wherein the material has an average particle size in the range of from 10 to 70 μm.

11. A process for surface treating a particulate antiperspirant material which comprises bringing the antiperspirant material into contact with an alkanolamine in a liquid medium and maintaining contact until at least some alkanolamine is deposited on or absorbed in the surface of the antiperspirant material.

12. A process according to claim 10 which comprises alkanolamine is contacted with the antiperspirant material in molten form or in solution.

13. An antiperspirant composition comprising an antiperspirant material and a liquid phase comprising a carrier wherein said the antiperspirant material comprises a particulate antiperspirant material which has been surface treated with an alkanolamine.

14. A composition according to claim 12 wherein the carrier comprises a polyglycol ether.

15. A composition according to claim 14 wherein the polyglycol ether comprises an ether of a polyethylene glycol, a polypropylene glycol or a polybutylene glycol.

16. A composition according to claim 15 wherein the polyglycol moiety contains from 5 to 24 glycol units.

17. A composition according to claim 14 wherein the polyglycol ether comprises polyglycol ether of a C3 to a C8 aliphatic alcohol.

18. A composition according to claim 17 wherein the alcohol is propanol or butanol.

19. A composition according to claim 18 wherein the polyglycol ether comprises a polypropylene glycol butyl ether containing from 10 to 16 polypropylene glycol units.

20. A composition according to claim 14 wherein the polyglycol ether constitutes from 5 to 95% by weight of the liquid phase.

21. A composition according to claim 14 wherein the polyglycol ether constitutes from 40 to 60% by weight of the liquid phase.

22. A composition according to claim 14 wherein the polyglycol ether and the alkanolamine are present in a weight ratio of from 30:1 to 120:1, preferably 45:1:80:1.

23. A composition according to claim 13 wherein the carrier contains a volatile or a non-volatile silicone oil.

24. A composition according to claim 23 wherein the liquid phase comprises 20 to 70% and preferably 40 to 70% by weight volatile silicone oil.

25. A composition according to claim 23 wherein the liquid phase contains from 0.01 to 0.1% by weight of a non-volatile silicone oil.

26. A composition according to claim 13 containing a clay or silica suspending agent.

27. A composition according to claim 26 wherein the suspending agent comprises from 2 to 6% by weight based on the composition of a hydrophobically treated clay.

28. A composition according to claim 13 comprising containing one or more suspension assistants, emollients or fragrances.

29. A composition according to claim 13 wherein the liquid phase constitutes from 90 to 50%, preferably 75 to 55% by weight and the particulate antiperspirant constitutes from 10 to 50%, preferably 25 to 45% by weight.

30. A composition according to claim 13 wherein from 95 to 1 parts, preferably 40 to 5 parts by weight of the composition is contacted with from 5 to 99 parts and preferably 60 to 95 parts by weight of a propellant to form an aerosol composition.

31. A composition according to claim 30 wherein from 40 to 5 parts by weight of the composition is contacted with from 60 to 95 parts by weight of the propellant to form the aerosol composition.

32. A method of controlling perspiration comprising topically applying to human skin a composition according to claim 14.

* * * * *